United States Patent [19]
Yamada et al.

[11] Patent Number: 4,895,029
[45] Date of Patent: Jan. 23, 1990

[54] METHOD OF AND APPARATUS FOR DETECTING DEFECTS OF ELASTIC-MEMBER JOINT PORTION

[75] Inventors: Seiki Yamada, Ibaraki; Akinori Kubota, Kobe, both of Japan

[73] Assignee: Sumitomo Rubber Industries, Ltd., Hyogo, Japan

[21] Appl. No.: 300,930

[22] Filed: Jan. 24, 1989

[30] Foreign Application Priority Data

Jan. 28, 1988 [JP] Japan .................................. 63-18332

[51] Int. Cl.$^4$ ............................................. G01N 3/08
[52] U.S. Cl. ........................................................ 73/827
[58] Field of Search ..................... 73/827, 150 A, 826, 73/828

[56] References Cited
U.S. PATENT DOCUMENTS 4,719,347 1/1988 Kugler et al. .................... 73/826 X

FOREIGN PATENT DOCUMENTS 269040 11/1988 Japan .................................... 73/826

Primary Examiner—Jerry W. Myracle
Attorney, Agent, or Firm—Birch, Stewart, Kolasch & Birch

[57] ABSTRACT

A method of and an apparatus thereof for detecting defects of a joint portion of an elastic-member sheet of the present invention comprises grasping an elastic-member sheet having a joint portion so as to detect at least one face of the joint portion through use of an optical measuring apparatus. With the elastic-member sheet being extended by a given percentage, comparing and identifying of the displacement amount of the joint portion, represented by a detecting signal, with a predetermined reference value by an operation processing unit which receives the detecting signal of the measuring apparatus so as to automatically judge the defect of the joint portion.

7 Claims, 14 Drawing Sheets

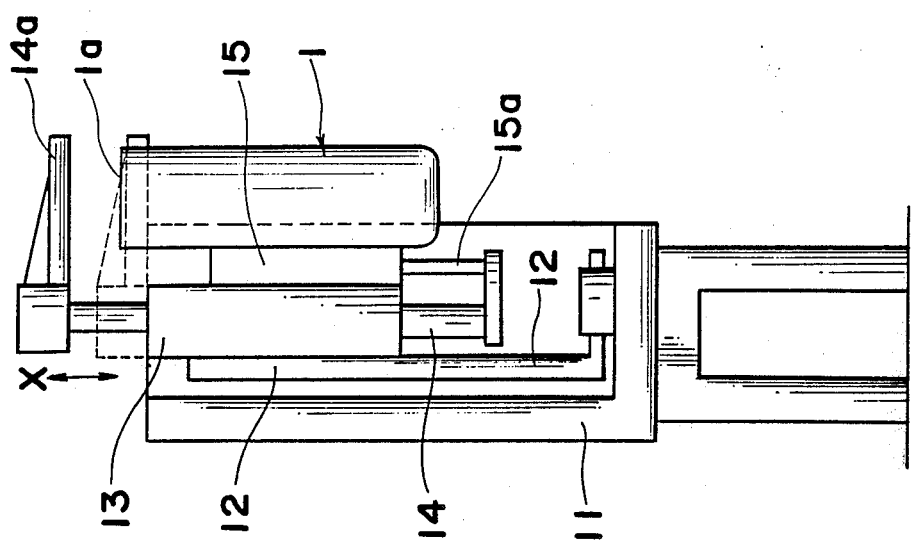
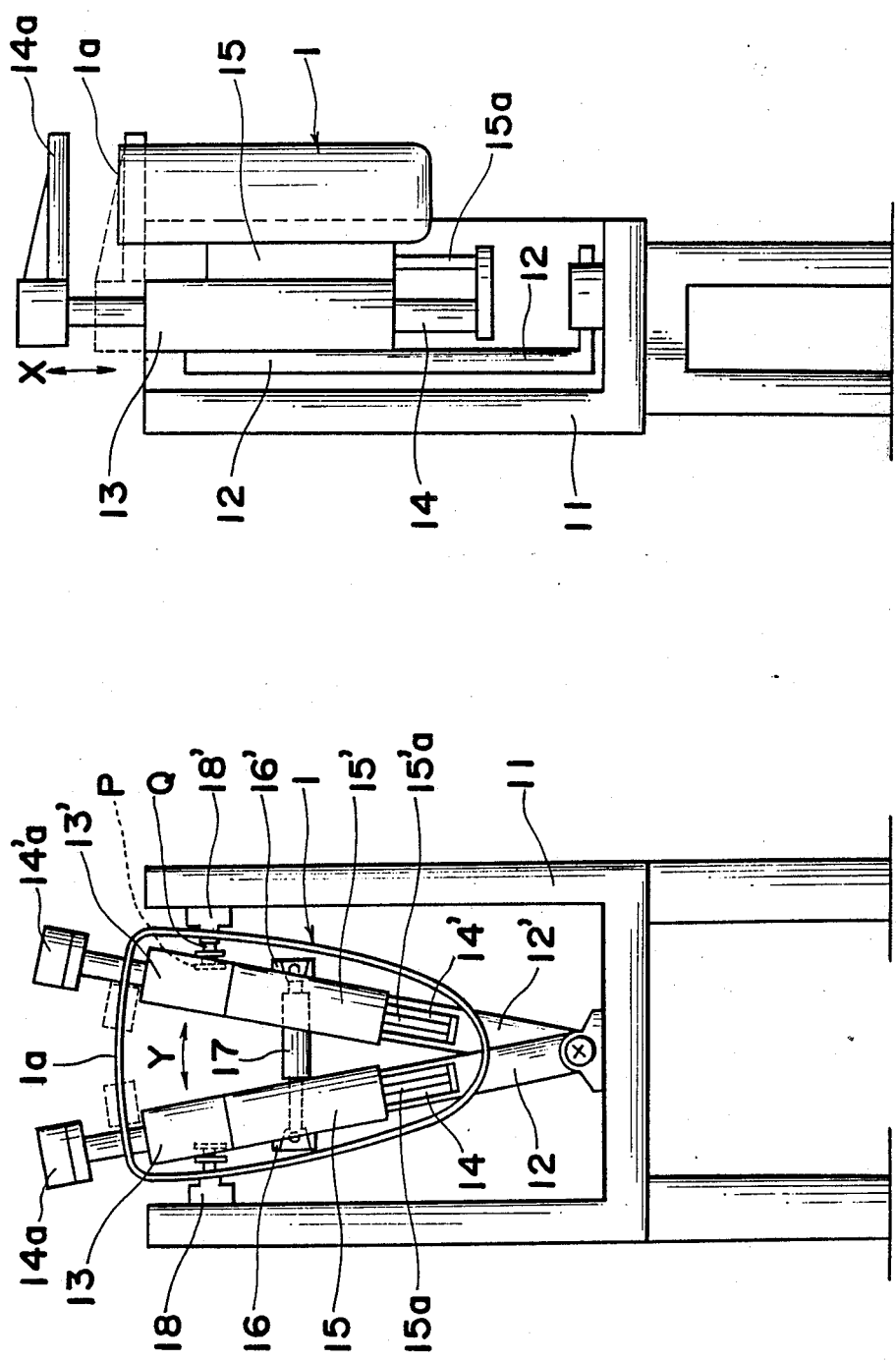

Fig. 7
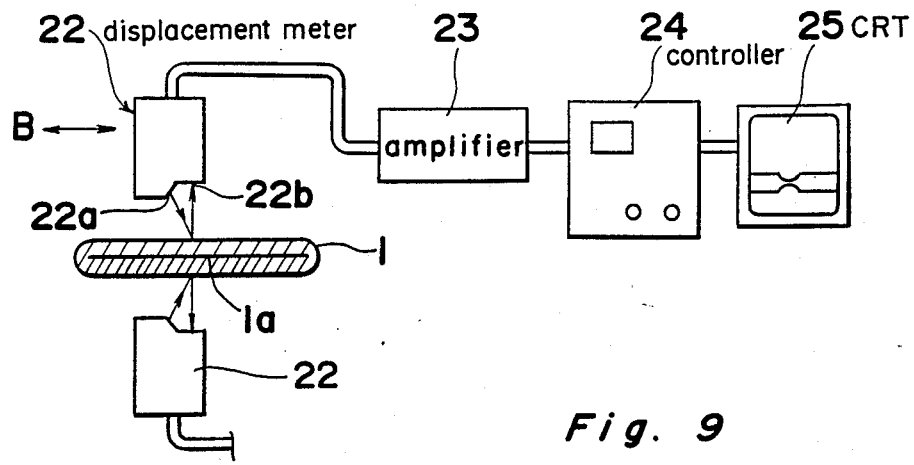
Fig. 8
Fig. 9
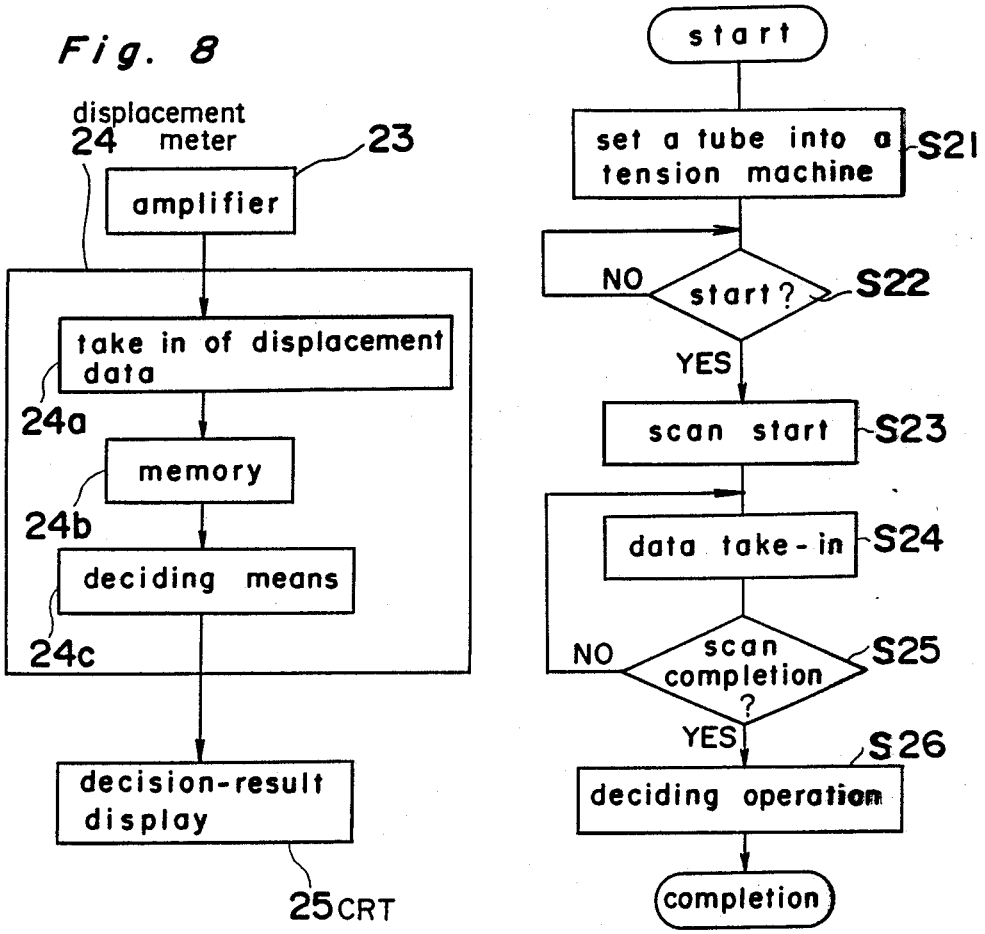

METHOD OF AND APPARATUS FOR DETECTING DEFECTS OF ELASTIC-MEMBER JOINT PORTION

BACKGROUND OF THE INVENTION

The present invention generally relates to a method of and an apparatus for optically and automatically detecting defects of a joint portion of an elastic-member sheet such as a tire tube or the like.

Conventionally, the splicing defect of a joint portion such as a tire tube joint is inspected by such a method as shown in FIG. 5(b). A defective splicing location 32, which is caused by talc biting, staggered splicing cure or the like in the joint portion 33 of a tire tube 31 of FIG. 5(a) comes out as being a dent in a pull condition. Both sides of the defective splicing location 32 are grasped by a sheet tension machine (not shown), so that the defective splicing location is dented through the pulling operation until the tire tube becomes approximately two through three times as long as before as shown by an arrow A in FIG. 5(b). An operator visually observes the upper surface 33a of the joint portion 33 directly and the reverse face 33b of the joint portion 33 directly through a mirror so as to judge whether or not the dent is defective in accordance with the experimental judgement of the operator.

However, the conventional method of inspecting the defects does not have universal validity in inspection, because the quality of the joint portion is judged by the experiment simply through the visual observation of the operator. The judgement reference is not quantitative, thus being vague under the control of personal subjectivity. Furthermore, because of the human visual inspection, longer time is ineffectively required for the inspection, and some oversights of the defective locations are unavoidable by mistake.

SUMMARY OF THE INVENTION

Accordingly, an essential object of the present invention is to provide a method of and an apparatus for detecting defects of an elastic-member sheet joint portion, which is capable of automatically measuring the displacement amount caused by the defective splicing of the joint portion of the elastic-member sheet without depending on human visual sight.

Another important object of the present invention is to provide a method of and an apparatus for detecting defects of an elastic-member sheet joint portion, which is capable of effective and efficient detection of the defective splicing of the elastic-member sheet in accordance with a universal reference through the automatic judgement of the measured results.

In accomplishing these and other objects, according to a preferred embodiment of the present invention, there is provided a method of detecting defects of an elastic-member sheet joint portion which comprises the steps of grasping an elastic-member sheet having a joint portion so as to extend it by a given percentage. At least one face of the extended elastic-member sheet joint portion is detected by a measuring apparatus through the use of an optical means. A detecting signal providing by the measuring apparatus is input into an operation processing unit and is compared and identified in the operation processing unit. The displacement amount of the dent or the like of the joint portion is represented by the detecting signal and is compared with reference values given previously so as to automatically judge the defects of the joint portion.

An apparatus for detecting devices of an elastic-member sheet joint portion comprises a sheet tension mechanism for grasping the elastic-member sheet with the joint portion in it so as to extend it by a given percentage, a measuring apparatus provided with a light emitting section and a light receiving section, positioned on at least one face of the joint portion of the extended sheet so as to detect the displacement amount of the dent or the like of the joint portion. An operation processing unit is used for comparing and identifying the displacement amount of the joint portion and its vicinity, represented by the detected signal inputted from the measuring apparatus, with previously given reference values so as to judge the defect of the joint portion, and adapted to output a processed detecting signal and a signal representing the judgement results.

In the apparatus for detecting defects of an elastic-member sheet joint portion of the present invention, both sides of the joint portion of the elastic-member sheet to be inspected are grasped by the sheet tension mechanism so as to extend the elastic-member sheet up to a given percent. When the joint portion and its vicinity are measured by a measuring apparatus disposed on at least one face of the joint portion, the displacement amount of the joint portion and its vicinity is provided as a detecting signal representing a dent amount or an area ratio of the shadow with respect to the whole picture face by lights transmitted from a light emitting section, reflected by the joint portion and its vicinity, and received by a light receiving section. The detecting signal is inputted into an operation processing apparatus. The operation processing apparatus compares and identifies the displacement amount of the joint portion and its vicinity represented by the inputted detecting signal with a previously given reference value so as to judge, for example, that there is defective splicing caused by talc bites or the like when a concave portion of the reference value or higher has been judged to exist. The detecting signal image-processed by the operation processing unit is outputted as an image, i.e., a line or shading representing the displacement amount, for example, into the display apparatus, and also, a signal representing the defective splicing which is a judgement result is outputted as a buzzer sound to, for example, a warning unit.

BRIEF DESCRIPTION OF THE DRAWINGS

These and other objects and features of the present invention will become clear from the following description taken in conjunction with the preferred embodiments thereof with reference to the accompanying drawings, in which:

FIGS. 6(a) and 6(b) are front and side views, each showing a tube tension machine to be employed in the apparatus of FIG. 1;

FIG. 7 is a schematic view of an apparatus for detecting defects of an elastic-member sheet joint portion in accordance with a second embodiment of the present invention;

FIG. 8 is a function block diagram of a controller employed in the apparatus of FIG. 7;

FIG. 9 is a flow chart showing the operation of the apparatus of the second embodiment;

DETAILED DESCRIPTION OF THE INVENTION

Figure 1:
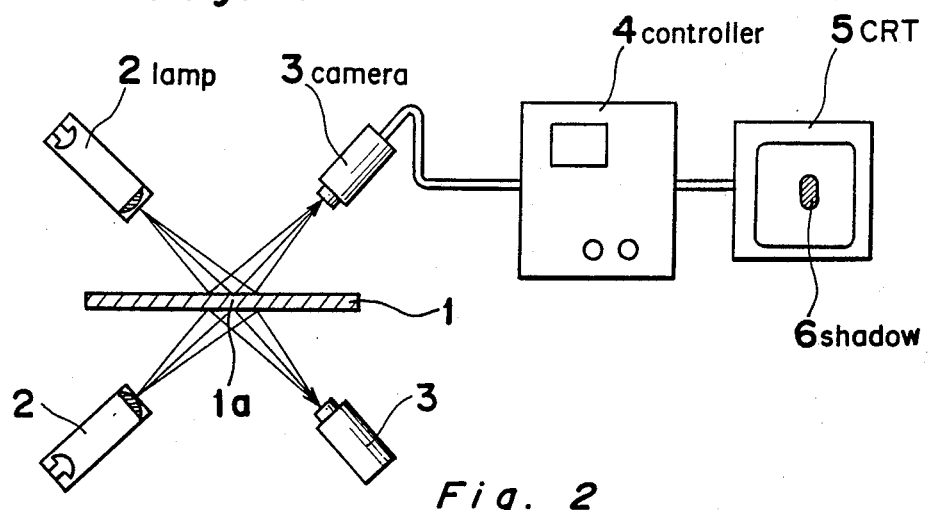
FIG. 1 is a schematic view showing an apparatus for detecting defects of an elastic-member sheet joint portion in accordance with a first embodiment of the present invention.

Before the description of the present invention proceeds, it is to be noted that like parts are designated by like reference numerals throughout the accompanying drawings.

Referring now to the drawings, there is shown in FIG. 1 an apparatus for use in a defect detecting method of a joint portion of an elastic-member sheet in accordance with a first embodiment of the present invention. The apparatus includes a tire tube 1 of an elastic-member sheet having a joint portion 1a, a lamp 2 as a light emitting means for projecting light onto the joint portion 1a of the tire tube 1, and a camera 3 for catching the reflected light from the joint section 1a and its vicinity so as to convert it into image signals. The apparatus further includes a controller 4 serving both as a signal inputting unit and an operation processing unit which has the lamp 2 and camera 3 mounted thereon so as to convert the picture image signal inputted from the camera 3 into binary-coded signals by a well known method. The controller is adapted to compare the area of the shadow 6 of the picture image signals with that of the entire picture face after the picture image signals have been enlarged and reduced into the given size so as to judge the joint portion 1a as being defective when the percentage thereof in the comparison has exceeded a reference value. The CRT 5 is included for displaying on the image face the binary-coded image signals of the shadow 6 to be outputted from the operation processing unit of the controller 4.

Figure 2:
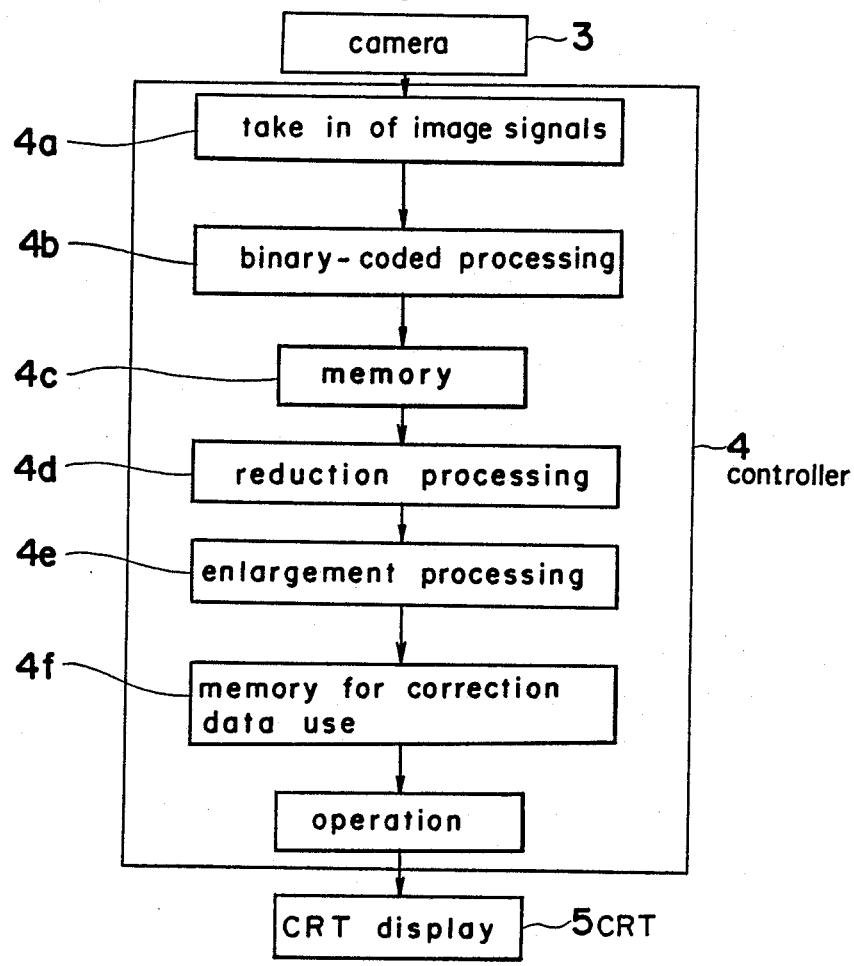
FIG. 2 is a functional block diagram of a controller employed in the apparatus of FIG. 1.

FIG. 2 shows a block diagram for the purpose of showing the function of controller 4. Namely, the controller 4 receives an image signal from the camera 3 so as to make it binary-coded, thereafter to store it in the memory 4c, then to reduce or enlarge the binary-coded data as described later, accommodate the processed data in the memory for correction data, to calculate them and to output the calculated results on the CRT 5.

Figure 5A:
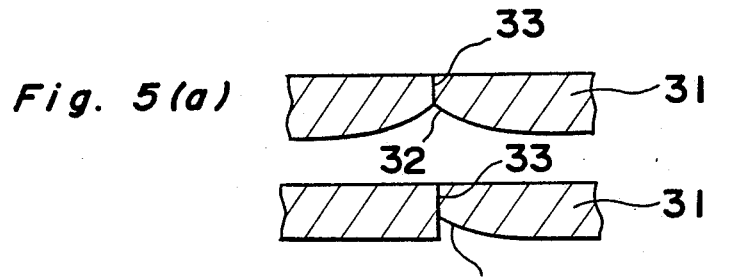
FIGS. 5(a) and 5(b) are cross-sectional views of a tire tube at times before and after the extension thereof.
Figure 5B:
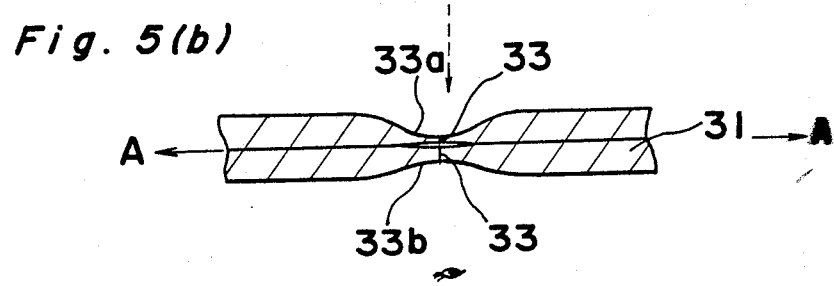

A sheet tension mechanism, as shown in FIG. 6, to be described later, is provided on both sides of the joint portion 1a of the tire tube 1. The apparatus for detecting the defects of the sheet provided together with the sheet tension mechanism is operated, with both side edges of the tire tube 1 being grasped by the sheet tension mechanism to extend the tire tube 1 until it becomes as long as approximately 120 through 300%, so as to detect the defects of the joint portion 1a of the tire tube 1. It is to be noted that the extension ratio for the tire tube 1 is in a range where the displacement amount (dent amount) of the joint portion 1a becomes maximum. The lamp 2, composed of a halogen lamp or the like, and the camera 3, composed of a CCD (charge coupled device), constitute a measuring apparatus with the angle of the light source 2 with respect to the camera 3 being so extended that the largest shadow 6 appearing on the CRT 5 may be provided in the dented or depressed joint portion 1a. Also, if the measuring apparatus, the controller 4 and the display apparatus 5, is disposed not only on the surface side 33a of the tire tube as shown in FIG. 5, but also on the reverse face side 33b, may efficiently detect at one time the defect of the joint portion 1a from both the front and reverse sides. When the joint portion 1a has been judged as being defective, the operation processing unit of the controller 4 outputs a signal representative of the judgement result to a warning unit (not shown) so as to generate a buzzer sound.

The operation of the first embodiment of the above-described construction will be described hereinafter with reference to the flow chart of FIG. 3, including one embodiment of a method for detecting defects of the joint portion 1a in accordance with the present invention.

To begin with, at step S1, both sides of the joint portion 1a of the tire tube 1 to be inspected are grasped by the sheet tension mechanism (see FIG. 6) so as to extend the tire tube 1 by approximately 120 through 300%. Then, when a start button is confirmed to have been depressed at step S2, the lamp 2 of a detecting apparatus disposed respectively at the front and reverse faces of the joint portion 1a is activated at step S3. Then, the camera 3 converts the displacement amount of the joint portion 1a and its vicinity into an image signal of light and dark, and the operation processing apparatus of controller 4 receives the image signal at step S4. The operation processing unit processes the inputted image signal into a binary code in accordance with a given reference at step S5 so as to accommodate the binary-coded data into the memory at step S6. Also, at steps S7 and S8, the data is enlarged and reduced to a given size, thereafter at step S9, the data after the processing is accommodated in a memory for correction data use, and at step S10, the ratio between the shadow area 6 and the area of the whole picture face is obtained. At step S11, if the area ratio of the shadow 6 is judged to be larger than the reference value, it is decided that the defective splicing in the joint portion 1a exists due to talc biting or staggered joint cure, as shown in FIG. 5, thereby outputting the binary-coded image signal to the display apparatus 5 so as to effect the display as shown in FIG. 1, and to cause the warning apparatus (not shown) to generate a buzzer sound. If the area ratio of the shadow 6 is judged to be smaller than the reference value, it is decided that the joint portion has no defective splicing and the binary-coded image signal is likewise outputted to the display apparatus 5 so as not to generate the buzzer sound.

Figure 3:
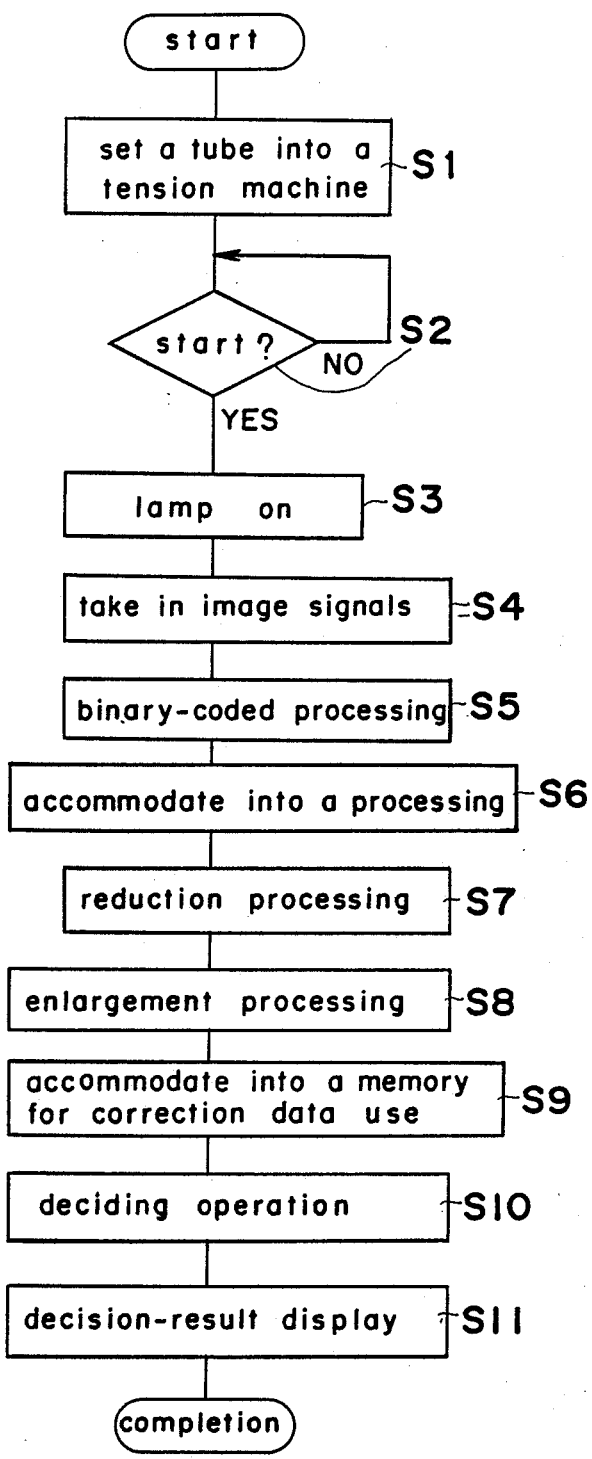
FIG. 3 is a flow chart showing the operation of the apparatus of the first embodiment.
Figure 4A:
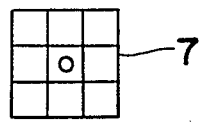
FIGS. 4(a) to 4(d) are illustrative views, each showing a skill of reduction and enlargement processing in connection with the operations of FIG. 3.
Figure 4B:
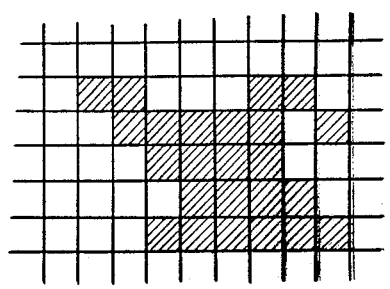
Figure 4C:
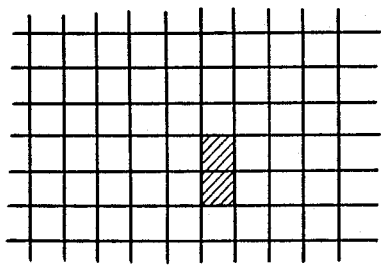
Figure 4D:
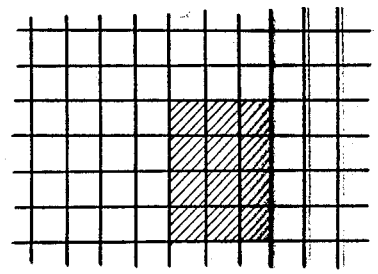

FIG. 4 shows graphs, each schematically illustrating the skill of the reduction processing or the enlarging processing at steps S7 and S8 of FIG. 3. When the image of the binary-coded signal at step S5 of FIG. 3 is the one as shown, for instance, in FIG. 4(b), such a filter 7 of elements disposed in a 3×3 fashion as shown in FIG. 4(a) is applied upon the image so as to bring attention to the central picture element of an image marked with a circle. In the reduction processing with interest in the picture element of a central circular mark of the filter, an AND operation which makes the central picture element a black ("1") is effected when all the surrounding picture elements are the black ("1") so as to obtain such an image as shown in FIG. 4(c). In the enlargement process, an OR operation which makes the central picture elements black is effected so as to obtain such an image as shown in FIG. 4(d).

In the first embodiment mentioned above, as the unevenness of the extended joint portion 1a is adapted to be inspected with the detecting apparatus being provided on both the front and reverse faces of the tire tube 1, the defective splicing location may be efficiently found at one time in the front and reverse faces of the joint portion 1a, thus resulting in better productivity. Also, when the operation processing unit of the control 4 has been judged to have the defective splicing in the joint portion 1a, the warning unit is so arranged as to sound a buzzer so that the operator does not overlook the defective location. In addition, the displacement amount of the joint portion and its vicinity may be displayed with binary-coded images on the display apparatus 5 independently of the favorable or unfavorable judgement results. Therefore, the operator has a strong advantage in that the operator is capable of passing judgement on the quality of the joint portion 1a by looking at the image at will. Also, as the defect of the joint portion 1a is so arranged as to be detected at its fully automatic operation with the driving means for the measuring apparatus comprising the lamp 2 and camera 3 and the controller, and the operation processing unit, it is needless to say that by far the most positive and efficient inspection may be performed, with the employment of the universal quality reference, than that of the conventional visual inspection.

It is to be noted that the measuring apparatuses 2 and 3 of the first embodiment may be effected by manual operation, instead of the automatic driving of the controller 4. In addition to the buzzer sound, a warning lamp or the like may also be used as warning upon detection of the defective location.

FIGS. 6(a) and 6(b) are a front face view and a side face view, each showing a tube tension machine or a sheet tension mechanism for extending the tire tube 1 to be inspected. The tube tension machine is rotatably mounted with the lower ends of two arms 12, 12' being pivoted at the center of the bottom portion of a box-shaped frame 11, whose front face and top face are open. Guide members 13, 13', into which rods 14, 14', having forwardly projecting tube grip portions 14a, 14'a at their top ends, are slidably inserted and are secured to the arms 12, 12'. The tip ends of the piston rods 15a, 15'a of two cylinders 15, 15' are respectively coupled to the lower ends of the rods 14, 14' so as to vertically move them as shown by arrow X. The cylinders 15, 15' are downwardly secured to each guide member, while with the basic end of a cylinder 17 located between the arms 12, 12' and the piston rod tip end thereof being coupled through the brackets 16, 16' and a pin to the arms 12, 12', the arms 12, 12' are oscillated as shown by arrow Y, Stoppers 18, 18' are for restricting oscillation of the arms 12, 12' and are secured to the right and left of the upper portion of the frame 11. The piston rods 15a, 15'a of the cylinders 15, 15' are projected, the tube grip portions 14a, 14'a of the rods 14, 14' are lowered so far as a position shown in broken lines of FIG. 6(b) in the direction of the arrow mark X. At this position, both sides of the joint portion 1a of the tire tube 1 are grasped and gripped by the grip portions 14a, 14'a, thereafter the piston rod of the cylinder 17 is projected so that the arms 12, 12' are pivoted until they come into contact against the stoppers 18, 18' on both sides, to the right and left in the direction of the arrow mark Y. The stoppers 18, 18' are so arranged as to adjust the projection degree of the tip end into two stages P and Q, so that the extension of 150% may be given to the tire tube 1 at a point P, and the extension of 200% at a point Q.

FIG. 7 is a schematic view showing a second embodiment of an apparatus for detecting defects of the present invention. In the second embodiment, an optical type displacement meter 22 which is provided with a light emitting section 22a and a light receiving section 22b is used as a measuring apparatus. The light which is projected from the light emitting section 22a is reflected by the joint portion 1a and its vicinity is received by the light receiving section 22b. The light is converted into detecting signals representative of the dent amount of the joint portion 1a by a light contact needle method, so that the detecting signal is so arranged as to be inputted into the controller 24 through an amplifier 23.

FIG. 8 is a block diagram for the purpose of showing the function of controller 24. Namely, the controller 24 receives the displacement data from the amplifier 23 so as to store it in the memory 24b. The controller then compares the flat portion near the tube joint with the dent amount (depth and width) of the concave or depressed portion in the operation processing unit in accordance with the displacement data, thereby deciding that there exists a defective splicing location when the dent amount has been judged to be more than a predetermined tolerance value. The controller then causes a warning unit to generate a buzzer sound. Also, the detecting signal is caused to be continuously outputted into the display apparatus 25, independently of the quality of the joint portion 1a, to display a curve corresponding to such a sectional shape of the extended joint portion 1a as shown in FIG. 8. Such an apparatus for detecting defects is disposed on both the front and reverse faces of the tire tube 1, as in the first embodiment, so as to effect the detection with the tire tube 1 being extended by approximately 120 through 300%.

The second embodiment is operated as shown in the flow chart of FIG. 9. Namely, suppose at step 22 a start button is judged to have been depressed, with a tire tube 1 to be inspected detected as being set at step 21 in the above-described tension machine in the same manner as shown in FIG. 6. The optical type displacement meter 22 is then driven by a driving apparatus, as shown in FIG. 10 and to be described later, in a direction normal to the joint portion 1a as shown with an arrow mark V, as well as in a direction along the joint portion 1a in the direction of an arrow mark Z, thereby starting the scanning at step S23. When it is judged that the displacement data is received in the memory 24b of the controller 24 at step S24, and the scanning has been completed at step S25, the suitability of the displacement data, i.e., the existence or absence of the defective splicing is decided at step S26.

Figure 10A:
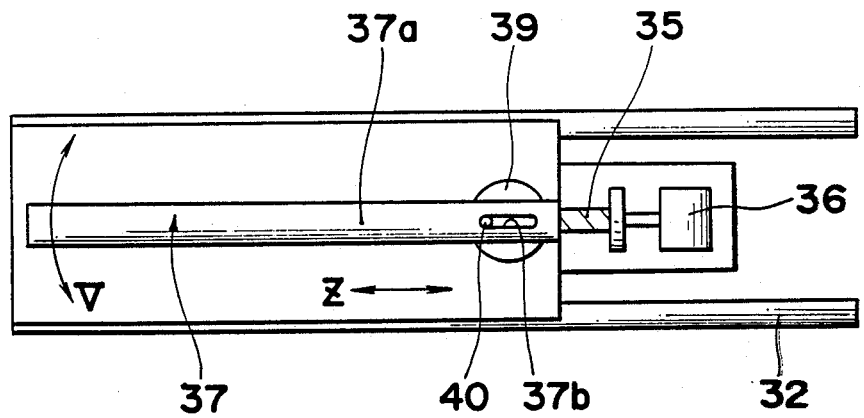
FIGS. 10(a) to 10(c) are a plan view, a side view and a front view of a driving apparatus for a displacement meter to be employed in the apparatus of FIG. 7.
Figure 10B:
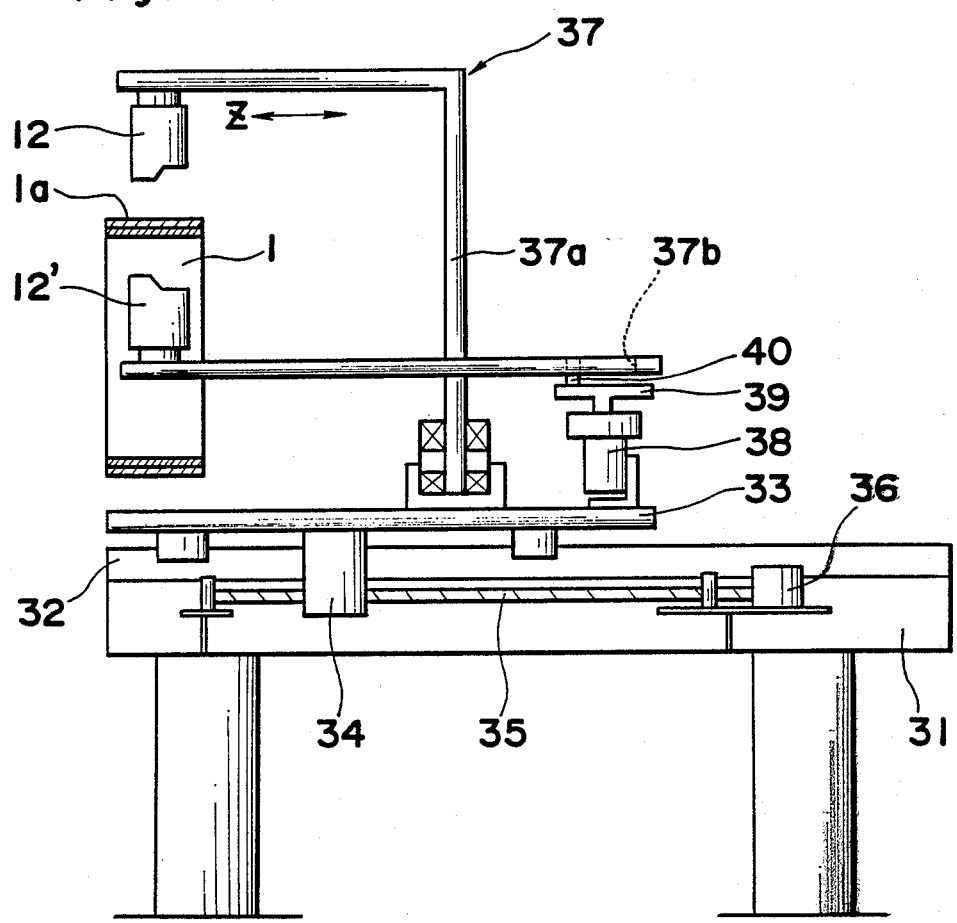
Figure 10C:
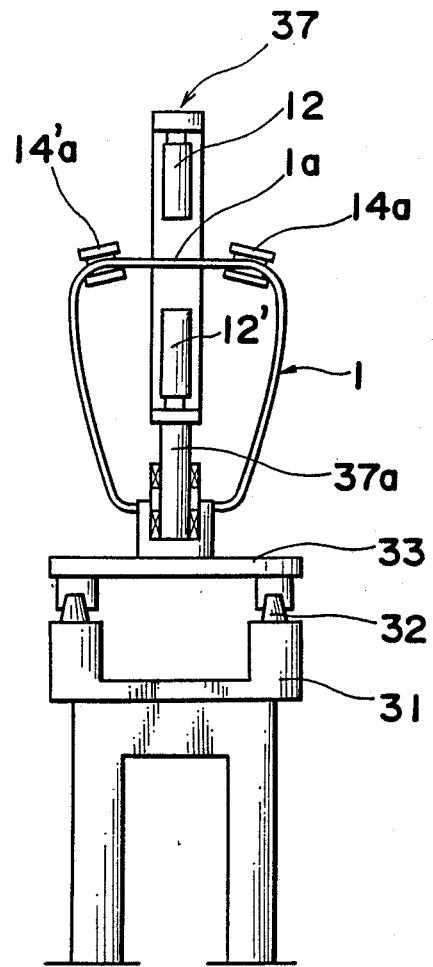
Figure 10D:
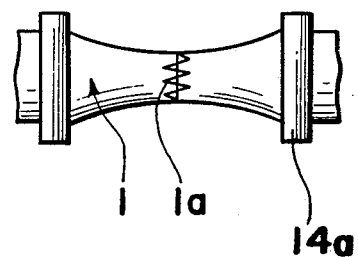
FIG. 10(d) is a plan view of a tube to be adapted.

FIGS. 10(a), 10(b) and 10(c) are respectively a plan view, a side view, a front face view of a driving apparatus for driving the optical type displacement meter 22 of FIG. 7 and FIG. 10(d) is a plan view of a tire tube extended. The driving apparatus has a moving platform 33 slidably placed on a linear guide 32 disposed on the top face of a frame 31. A motor 36 is rotated with a ball screw 35 engaged with a ball nut 34 secured to the bottom portion of the moving platform 33 so as to reciprocate the moving platform 33 in the direction of an arrow marked 2. A ]-shaped support frame 37 is pivotally supported, by the lower end of its vertical shaft 37a, on the top face of the moving platform 33 so as to confront its ends of the support frame 37 to secure optical type displacement meters 12, 12'. An eccentric pin 40 projected from a rotary disc 39, driven by a motor 38, is engaged into a long hole 37b drilled at the rear end of a support frame 37, so that the tip ends of the support frame 37 are adapted to be oscillated in a width of 20 through 30 mm in the direction of an arrow mark V. The joint portion 1a of the tube 1 which is extended and grasped by the tube grip portions 14a, 14'a of a tube tension machine in the same manner as shown in FIG. 6 is disposed, as shown in FIGS. 10(b) and 10(c), between the opposite optical type displacement meters 12, 12'. By the oscillation of the support frame 37 from side to side and the longitudinal movement of the moving platform 33 from front to back, the joint portion 1a is scanned in a zigzag manner as a result of these movements.

Figure 11:
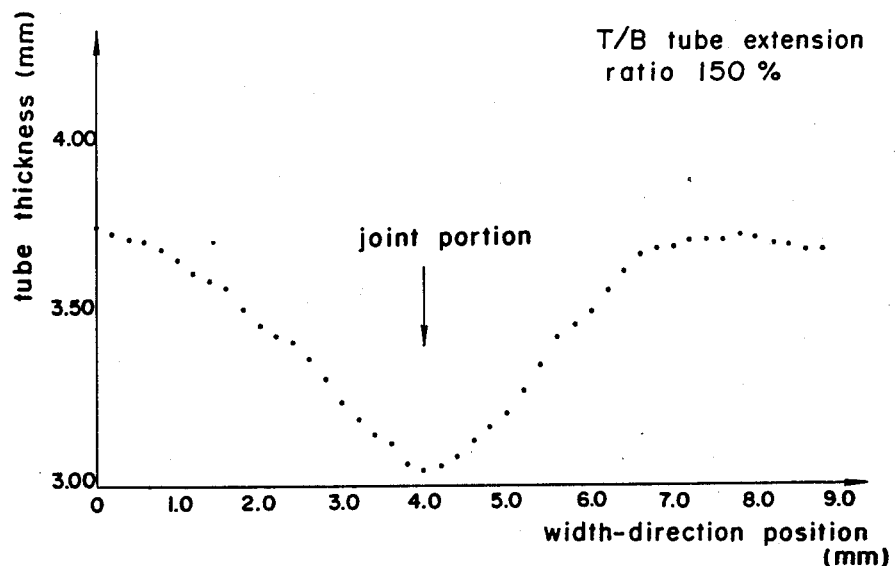
FIGS. 11 through 14 are graphs, each showing one example of the measured result of the tube thickness in the second embodiment of FIG. 7.
Figure 12:
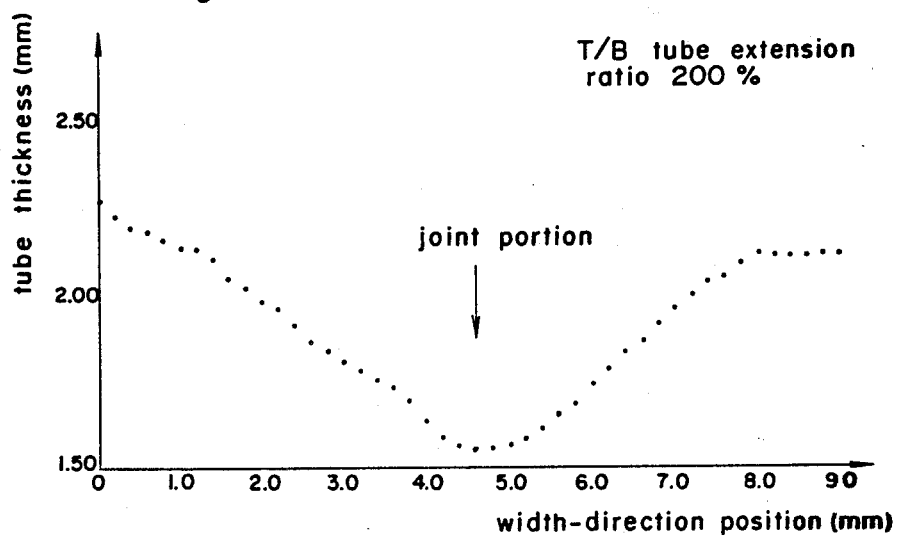
Figure 13:
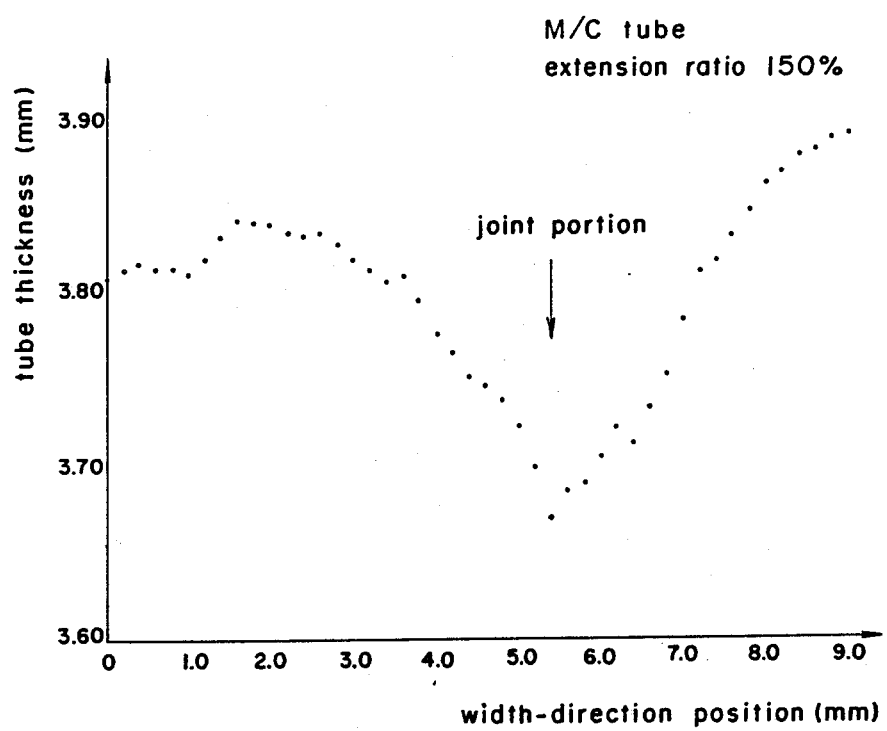
Figure 14:
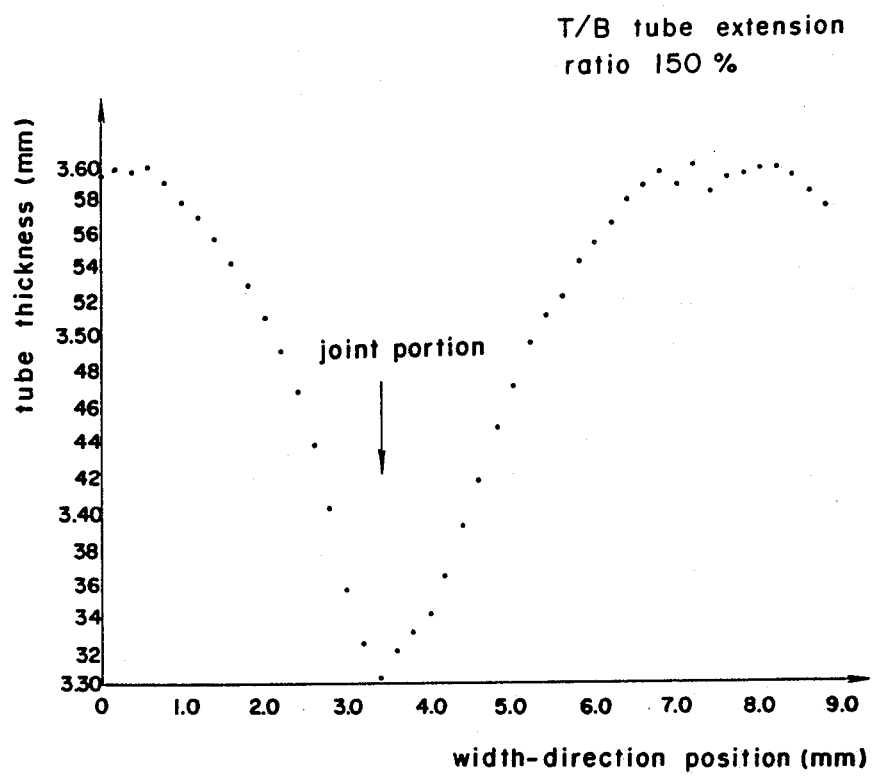

FIGS. 11 through 14 are graphs, each showing one example of the measurement result of the tube thickness in the second embodiment. FIGS. 11 and 12 are the measurement results when the tube for truck or bus use has been respectively extended by 150% and 200%, while FIGS. 13 and 14 are the measurement results when the tube for motorcycle use has been respectively extended by 150% and 200%. The measurement is effected at a pitch of 0.2 mm through the movement of-ments.

FIGS. 11 through 14 are graphs, each showing one example of the measurement result of the tube thickness in the second embodiment. FIGS. 11 and 12 are the measurement results when the tube for truck or bus use has been respectively extended by 150% and 200%, while FIGS. 13 and 14 are the measurement results when the tube for motorcycle use has been respectively extended by 150% and 200%. The measurement is effected at a pitch of 0.2 mm through the movement of the optical displacement meter 22 approximately 5 mm by 5 mm onto both sides in the direction of an arrow marked B around the joint portion 1a shown in FIG. 7. As is clear from the drawing, the dent in the joint portion 1a is larger, with the extension ratio of 150% being provided in the tube for truck or bus use, while it is larger, with the extension ratio of 200% being provided in the tube for motorcycle use. Accordingly, as there is a natural extension ratio where the dent in the joint portion considerably appears in accordance with the type of tire, it is found that inspection by the defect detecting apparatus as in the second embodiment is preferably effected under the extension ratio of a larger dent content.

The second embodiment is basically the same in measurement principle and construction as the above-described first embodiment. Accordingly, the second embodiment has an advantage in that the light-emitting section and the light-receiving section may be compactly integrated. Although the second embodiment has a disadvantage of having a narrower inspection region than the first embodiment.

Figure 15:
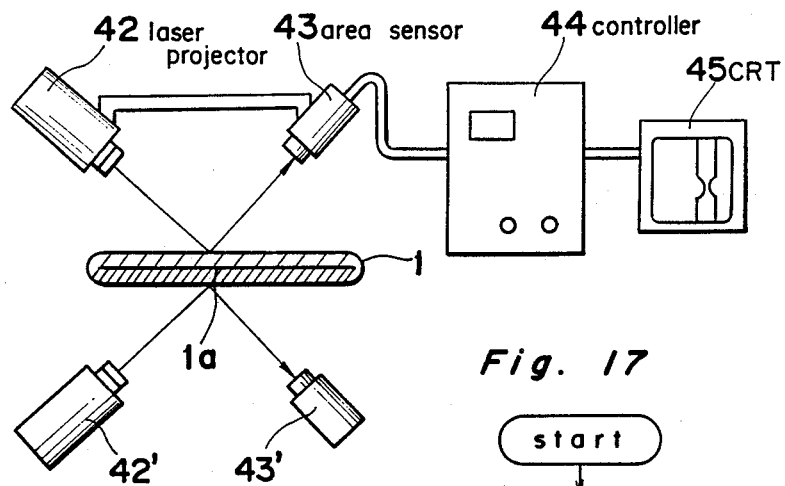
FIG. 15 is a schematic view showing an apparatus for detecting defects of an elastic-member sheet joint portion in accordance with a third embodiment of the present invention.
Figure 18:
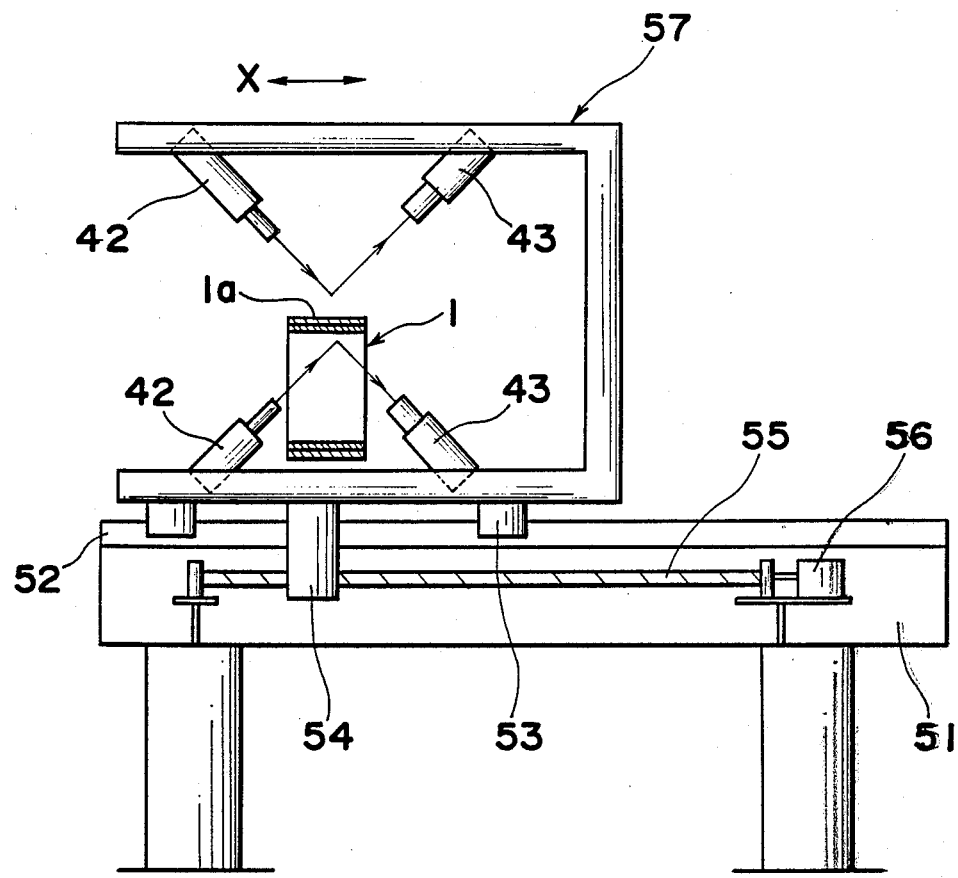
FIG. 18 is a side view of a moving platform employed in the apparatus of the third embodiment.

FIG. 15 is a schematic view showing the third embodiment of a defect detecting apparatus of the present invention. In the third embodiment, a laser projector 42 used as a light-emitting section and an area sensor 43 composed of a CCD or the like used as a light-receiving section are respectively mounted on a moving platform, as shown in FIG. 18, as a measuring apparatus at such an optimum angle where the dent amount appearing on a display apparatus 45 becomes maximum. Reflection light received by the area sensor 43 is converted into a detecting signal representative of streak patterns corresponding to the unevenness of the joint portion 1a by a conventional light cutting method through the driving of the moving platform in a direction along the joint portion 1a by a controller 44 so as to input the detecting signal it into the controller 44.

Figure 16:
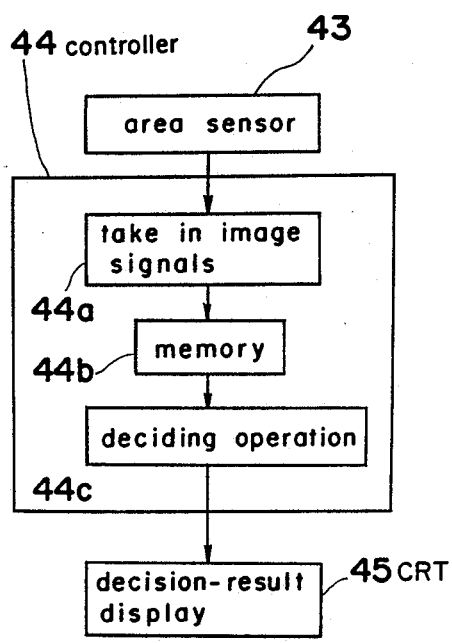
FIG. 16 is a function block diagram of a controller employed in the apparatus of FIG. 15.

FIG. 16 is a block diagram for the purpose of showing the function of the controller 44. Namely, the controller 44 receives a detection signal, i.e., the image signal from the area sensor 43 as digital data to store it into a memory 44b, compares the dent amount of the tube joint 1a in an operation processing section with the flat portion in accordance with the digital data so as to decide that there is a defective splicing location. When the dent amount has been judged to be more than a predetermined value, a warning unit is caused to generate a buzzer sound. The controller also outputs the detecting signal to the display apparatus 45 in a continuous manner independently of a good or bad joint portion so as to display such a curve as shown. The apparatus for detecting defects in the third embodiment is also disposed on both the front and reverse faces of the tire tube 1 being detected under a condition where the tire tube 1 is extended by approximately 120 through 300%.

Figure 17:
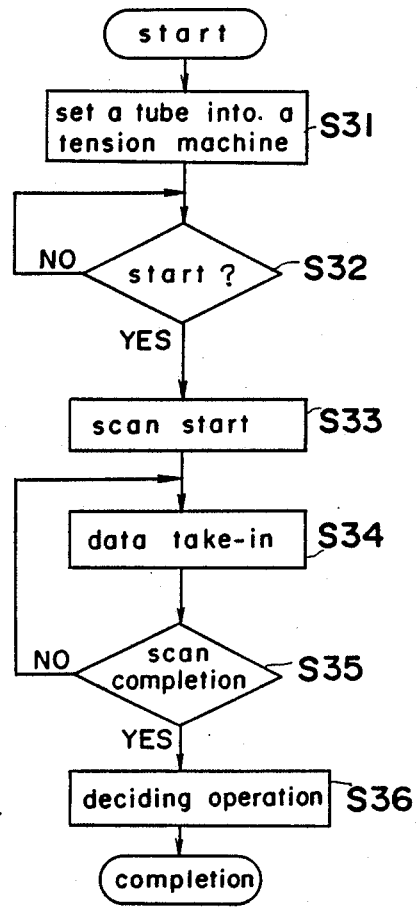
FIG. 17 is a flow chart showing the operation of the apparatus of the third embodiment.

The third embodiment is operated as shown in the flow chart of FIG. 17. Namely, to begin with, when it is judged that the tire tube 1 to be inspected is set in the above-described tension machine, as shown in FIG. 6, at step S31, and the start button has been depressed at step S32, the laser projector 42 and the area sensor 43 are driven along the joint portion 1a by a driving apparatus, as shown in FIG. 18 and to be described later, to start the scanning at step S33. The image data of a given width including the joint portion 1a is received in the memory of the controller 44 at step S34, and the scanning is judged to have been completed at step S35, so that the quality of the image data, i.e., the existence or absence of the defective splicing is decided at step S36.

FIG. 18 is a side view of a driving apparatus for driving the laser projector 42 and the area sensor 43 of FIG. 15. The driving apparatus has a moving platform 53 slidably placed on a linear guide 52 disposed on the top face of the frame 51, and a ball screw 55 engaged with a ball nut 54 secured to the bottom portion of the moving platform is rotated by a motor 56 so as to reciprocate the moving platform 53 in the direction of the arrow marked X. A ]-shaped support frame 57 is vertically placed on the top face of the moving platform 53, with laser projectors 42 and area sensors 43 being secured on the upper and lower sides of the support frame 57. The joint portion 1a of the tube 1 grasped by a tube tension machine, as shown in FIG. 6, is disposed between the upper and lower sides so that the joint portion 1a is adapted to be scanned through the longitudinal movement of the moving platform 53.

Figure 19A:
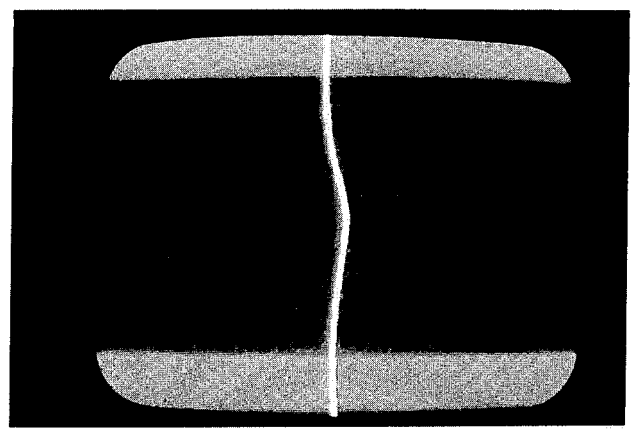
FIGS. 19(a) to 19(c) and FIGS. 20(a) to 20(c) are photographs, each showing an image being displayed on the display apparatus employed in the apparatus of the third embodiment.
Figure 19B:
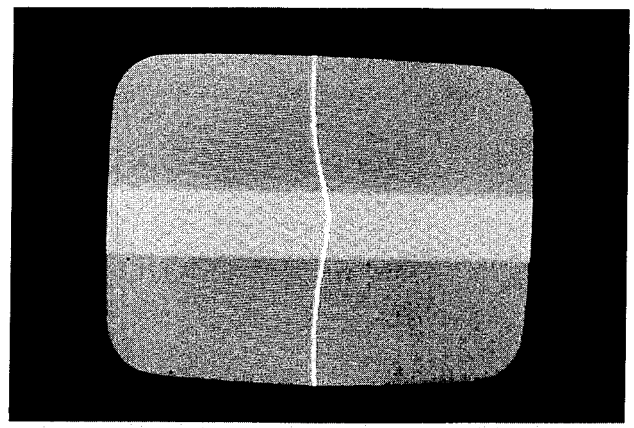
Figure 19C:
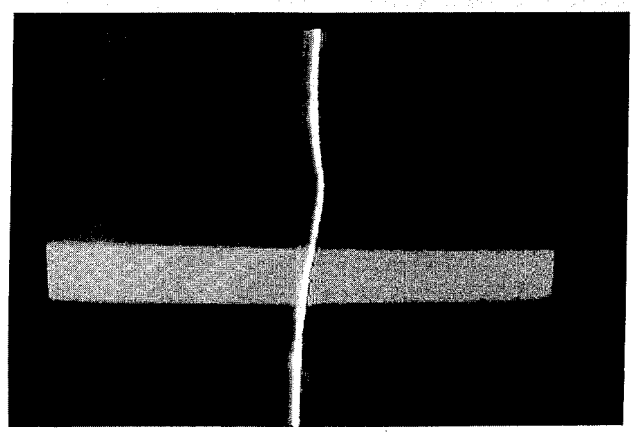
Figure 20A:
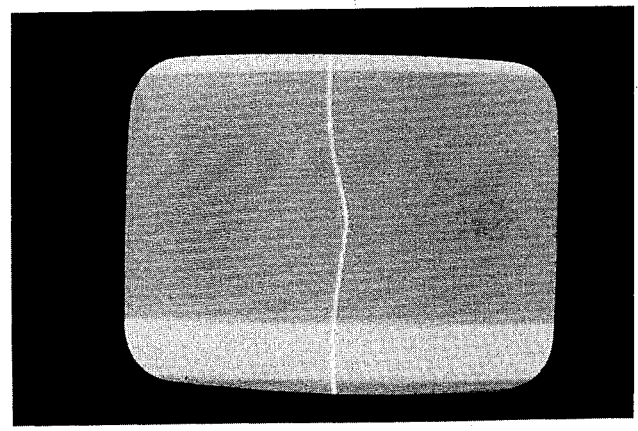
Figure 20B:
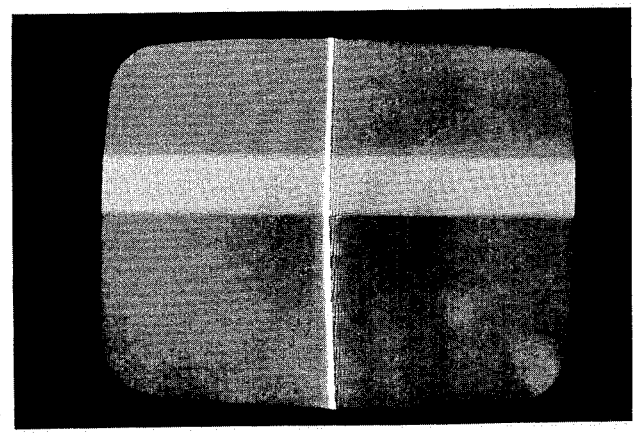
Figure 20C:
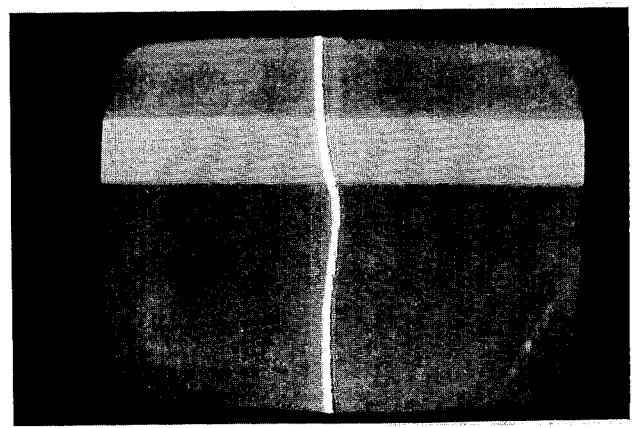

FIGS. 19 and 20 are views showing one example of an image displayed on a display apparatus 45 in the third embodiment. Reference characters θ, f in each drawing respectively show an incidence angle of the laser light and a focus distance of the laser projector 42. As is clear from FIGS. 19 and 20, the image of the joint portion with a dent caused therein has a dent in the joint portion 1a which should be a straight line as shown in FIGS. 19(a), 19(b) and 20(a). When the dent amount becomes more than a reference amount, the buzzer is sounded.

The third embodiment is, also, fundamentally the same in measuring principle and construction as the first embodiment. Accordingly, the third embodiment has an advantage in that it achieves an effect similar to that of the first embodiment, and is capable of passing more quantitative and positive quality judgement that the method of comparing the shadow areas through a binary-coded processing as in the first embodiment. When the detection is effected from the single face of the elastic-member sheet, the tube is required to be reversed, as in the case where the section shape of a tube or the like is annular, for effecting detection about the reverse face.

It is needless to say that the present invention is not restricted to the respective embodiments, and the elastic-member sheets are not restricted to the tire tubes.

As is clear from the foregoing description, according to the arrangement of the present invention, a method of detecting defects of a joint portion in an elastic-member sheet comprises the steps of grasping an elastic-member sheet having a joint portion so as to detect at least one face of the joint portion by a measuring apparatus through an optical means. With the elastic-member sheet being extended by a given percentage, comparing and identifying of the displacement amount of the joint portion represented by a detecting signal with a predetermined reference value by an operation processing unit which receives the detecting signal of the measuring apparatus is effected so as to automatically judge the defects of the joint portion. An apparatus for detecting defects in the elastic-member sheet joint portion of the present invention is provided with a sheet extending mechanism, a measuring apparatus, and an operation processing unit necessary for the embodiment of the above-described method. The system of the present invention is capable of automatically measuring the unevenness of the joint portion, instead of visually passing human judgement as previously, so as to automatically judge the quality of the measuring results for positively and efficiently detecting the defective splicing of the joint portion in accordance with the universal reference. Thus, it is possible to inspect the joint portion in the elastic-member sheet with considerably superior effects.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A method of detecting defects of an elastic-member sheet joint portion comprising the steps of:
   grasping the joint portion of the elastic-member sheet so as to extend it by a given percentage;
   detecting a property of at least one face of the joint portion of the extended elastic-member sheet by a measuring apparatus which includes an optical means;
   inputting a detecting signal from the measuring apparatus into an operation processing unit; and
   comparing and identifying, with a given reference value, a displacement amount of the joint portion represented by the detecting signal in the operation processing unit so as to automatically judge the defect of the joint portion.

2. A method of detecting defects of an elastic-member sheet joint portion in accordance with claim 1, wherein said displacement amount is an area, in size, of the shadow appearing on the image face of the joint portion.

3. A method of detecting defects of an elastic-member sheet joint portion in accordance with claim 1, wherein said displacement amount is a dent amount of the joint portion.

4. An apparatus for detecting defects of an elastic-member sheet joint portion comprising:
   a sheet tension mechanism for grasping an elastic-member sheet having a joint portion so as to extend it by a given percentage;
   a measuring apparatus, provided with a light-emitting section and a light-receiving section, disposed on at least one face of the joint portion of the extended sheet so as to detect a property of the joint portion and its vicinity; and
   an operation processing apparatus for comparing with a given reference value, and identifying, a displacement amount of the joint portion and its vicinity represented by a detecting signal inputted from the measuring apparatus so as to judge the defect of the joint portion, and also, to output a signal representing the judgement results.

5. An apparatus for detecting defects of an elastic-member sheet joint portion in accordance with claim 4, wherein the displacement amount is an area, in size, of the shadow appearing on the image face of the joint portion.

6. An apparatus for detecting defects of an elastic-member joint portion in accordance with claim 4, wherein the displacement amount is a dent portion of the joint portion.

7. An apparatus for detecting defects of an elastic-member sheet joint portion comprising:
   a sheet tension mechanism for grasping both sides of the joint portion of the elastic-member sheet to be inspected so as to extend the elastic member sheet up to a given percentage;
   a measuring apparatus, disposed on at least one face of the joint portion and including a light-emitting section and a light-receiving section, for detecting a property of the joint portion and its vicinity in a manner that a displacement amount of the joint portion and its vicinity is detected as a dent amount or a detecting signal representing an area ratio of the shadow with respect to the whole picture face by light transmitted from the light-emitting section, reflected by the joint portion and its vicinity, and received by the light receiving section;

an operation processing apparatus, for inputting the detecting signal from the measuring apparatus to compare and identify the displacement amount of the joint portion and its vicinity represented by the inputted detecting signal with a previously given reference value so as to judge that a defective splicing caused by talc bites is provided in the joint portion when a concave portion of the reference value has been judged to exist; and a display apparatus for inputting the detecting signal from the operation processing apparatus to output an image representing the displacement amount.

* * * * *